United States Patent
Moorman et al.

(10) Patent No.: US 9,839,364 B2
(45) Date of Patent: Dec. 12, 2017

(54) VENTRICULAR ACTIVATION (RR) ENTROPY CHANGE AS A PREDICTOR OF SUDDEN CARDIAC DEATH IN CARDIAC RESYNCHRONIZATION THERAPY PATIENTS

(71) Applicants: University of Virginia Patent Foundation, Charlottesville, VA (US); The Johns Hopkins University, Baltimore, MD (US)

(72) Inventors: J. Randall Moorman, Keswick, VA (US); Douglas E. Lake, Charlottesville, VA (US); Gordon F. Tomaselli, Lutherville, MD (US); Deeptankar Demazumder, Baltimore, MD (US)

(73) Assignees: University of Virginia Patent Foundation, Charlottesville, VA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/400,408

(22) PCT Filed: May 11, 2013

(86) PCT No.: PCT/US2013/040677
§ 371 (c)(1),
(2) Date: Nov. 11, 2014

(87) PCT Pub. No.: WO2013/170232
PCT Pub. Date: Nov. 14, 2013

(65) Prior Publication Data
US 2015/0133807 A1    May 14, 2015

Related U.S. Application Data

(60) Provisional application No. 61/645,830, filed on May 11, 2012.

(51) Int. Cl.
*A61B 5/024* (2006.01)
*A61B 5/04* (2006.01)
(Continued)

(52) U.S. Cl.
CPC ........ *A61B 5/02405* (2013.01); *A61B 5/0006* (2013.01); *A61B 5/04012* (2013.01); *A61B 5/0456* (2013.01)

(58) Field of Classification Search
CPC .............. A61B 5/02405; A61B 5/0006; A61B 5/04012; A61B 5/0456
See application file for complete search history.

(56) References Cited

U.S. PATENT DOCUMENTS 6,216,032 B1    4/2001    Griffin et al.
2002/0052557 A1    5/2002    Griffin et al.
(Continued)

FOREIGN PATENT DOCUMENTS

WO    2010/077997 A2    7/2010

OTHER PUBLICATIONS

Costa et al., "Multiscale entropy analysis of biological signals," Physical Review E 71, Feb. 18, 2005, 021906-1-18, The American Physical Society.
(Continued)

*Primary Examiner* — Joseph Dietrich
(74) *Attorney, Agent, or Firm* — Vorys, Sater, Seymour and Pease LLP; Vincent M DeLuca (57) ABSTRACT

A method of determining health and mortality includes obtaining a ventricular activation (RR) time series from a subject for multiple temporal intervals. The method also includes calculating a cardiac entropy in the RR time series over the temporal intervals using coefficient of sample entropy (COSEn). Additionally, the method includes comparing the cardiac entropy between the intervals to deter-
(Continued)

mine health and mortality. The absolute and relative changes in entropy over a patient's follow up period provide dynamic information regarding health and mortality risk. The determination of health and mortality can then be used to create a treatment plan for the subject.

27 Claims, 8 Drawing Sheets

(51) Int. Cl.
*A61B 5/0456* (2006.01)
*A61B 5/00* (2006.01)

(56) References Cited

U.S. PATENT DOCUMENTS

| | | |
|---|---|---|
| 2007/0066906 A1 | 3/2007 | Goldberger et al. |
| 2009/0192394 A1 | 7/2009 | Guttag et al. |
| 2010/0056940 A1 | 3/2010 | Moorman et al. |
| 2010/0324436 A1 | 12/2010 | Moorman et al. |
| 2011/0306845 A1 | 12/2011 | Osorio |

OTHER PUBLICATIONS

Lake et al., "Sample entropy analysis of neonatal heart rate variability," Am J Physical Regul Integr Comp Physiol 238: R789-R797, Sep. 2002.

Varotsos et al., "Identifying sudden cardiac death risk and specifying its occurrence time by analyzing electrocardiograms in natural time," Applied Physics Letters 91, 2007.

Palus et al., "Entropies, Partitionings and Heart Rate Variability," Activitas Nervosa Superior, Jun. 1, 2009. pp. 65-72, vol. 51, No. 2.

VENTRICULAR ACTIVATION (RR) ENTROPY CHANGE AS A PREDICTOR OF SUDDEN CARDIAC DEATH IN CARDIAC RESYNCHRONIZATION THERAPY PATIENTS

CROSS-REFERENCE TO RELATED APPLICATIONS AND CLAIM FOR PRIORITY

This application claims priority under 35 U.S.C. §119(e) from U.S. application Ser. No. 61/645,830 filed May 11, 2012. This application is related to copending U.S. application Ser. No. 12/594,842 filed Oct. 6, 2009, and Ser. No. 12/866,056 filed Aug. 4, 2010, incorporated herein by reference in their entireties.

GOVERNMENT SPONSORSHIP

This invention was made with government support under NIH HL RO1 091062 awarded by the National Institutes of Health. The government has certain rights in the invention.

FIELD OF THE INVENTION

The present invention relates generally to cardiology. More particularly, the present invention relates to the dynamic analysis of cardiac rhythm to predict morbidity and mortality.

BACKGROUND OF THE INVENTION

Electrocardiograms have long been studied in order to analyze cardiac function and predict health, disease and mortality. In many cases, linear methods in the time and frequency domains are used to analyze the information from the electrocardiogram. One such linear method, is referred to as heart rate variability (HRV). In time domain analysis, a range of normal values for HRV analyzed in the time domain, frequency domain and geometrically are established based on 24-hour ambulatory recordings. Similar metrics, particularly in the time domain, are not universally accepted for short-term recording so stratification of continuous data can be used.

In contrast to time domain analyses, that do little to account for irregularities, the irregularity in the time-sampled intervals of electrocardiographic ventricular activation (RR) can be accounted for in frequency domain analyses in order to calculate an estimate of the power spectrum density (PSD). Because the typical PSD estimators implicitly assume equidistant sampling, the interval time series is for example, first converted to equidistantly sample a series using a cubic spline interpolation method to avoid generating additional harmonic components in the spectrum.

PSD estimations are performed as a method of cardiac assessment using the FFT (Welch's periodogram) and the parametric maximum-entropy "forward-backward linear least squares" autoregressive (AR) methods. In the FFT method, spectrum powers are calculated by integrating the spectrum over the frequency bands. In contrast, the parametric AR method models the time series as a linear combination of complex harmonic functions, which include pure sinusoids and real exponentials as special cases, and fits a function of frequency with a predefined number of poles (frequencies of infinite density) to the spectrum. The AR method asserts that the position and shape of a spectral peak is determined by the corresponding complex frequency and that the height of the spectral peak contains little information about the complex amplitude of the complex harmonic functions. In the AR method, the spectrum is divided into components and the band powers are obtained as powers of these components.

There are several fundamental limitations to all forms of frequency domain analyses. Nonstationarity in time series severely limits the range of frequencies that can be studied by all methods of frequency-domain analyses. Frequency-domain analyses, while retaining some information relating to ordering of observations, conceal details of interactions between mechanisms. (e.g., respiration-mediated change in heart rate may stimulate other mechanisms). Heart rates have "self-similar" fluctuations, affected not only by the most recent value but also by much more remote events, or in other words, a "memory" effect. In time series, these phenomena may be quantified as a repetitive pattern of fluctuation, but in the frequency domain, it may be indistinguishable from uncorrelated fluctuations.

Nonlinear dynamic analyses are an alternate approach for understanding the complexity of biological systems. By definition, a nonlinear system has an output that is simply "not linear," i.e., any information that fails criteria for linearity, i.e., output is proportional to input (e.g., Ohm's law), and superposition (behavior predicted by dissecting out individual input/output relationships of sub-components).

Figure 1A:
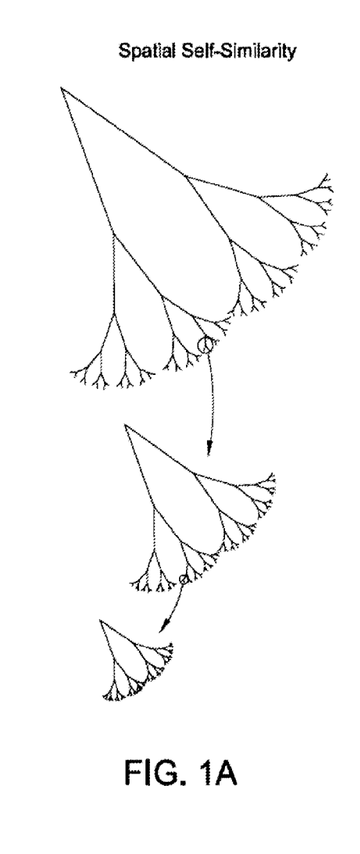
FIG. 1A illustrates fractal temporal processes of a healthy RR according to an embodiment of the present invention.
Figure 1B:
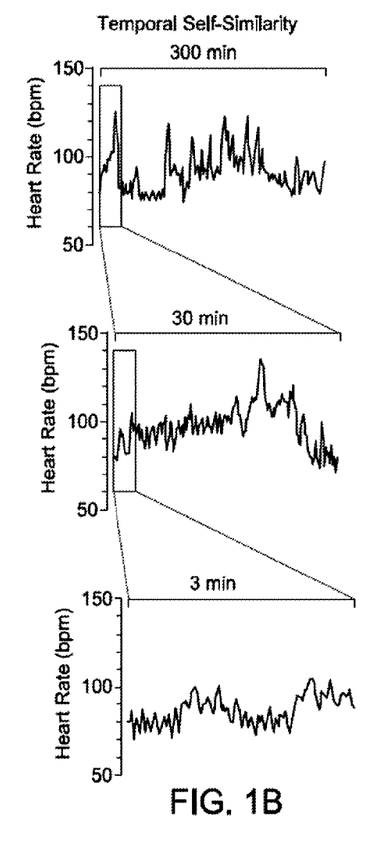
FIG. 1B illustrates wavelet analysis of healthy RR time series of >1500 beats (x-axis is time, y-axis is wavelet scale (5 to 300 secs) according to an embodiment of the present invention.
Figure 1C:
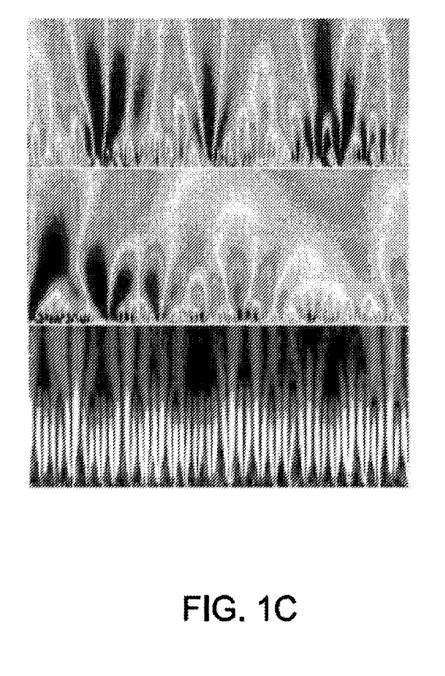
FIG. 1C illustrates the wavelet amplitudes according to an embodiment of the present invention.

Virtually all biological signals demonstrate nonlinear properties. A simple common example is nonstationarity (e.g., drift in heart rate or blood pressure during sleep-wake cycles). Although a variety of stationarity tests provide useful measures, some arbitrary criteria are needed to judge stationarity including statistical properties and relevant time scale. Moreover, important information on pathological states and natural processes (e.g., aging) is contained within the nonstationary properties of biological signals, as illustrated in FIGS. 1A-1C. FIG. 1A illustrates fractal temporal processes of a healthy RR. FIG. 1B illustrates wavelet analysis of healthy RR time series of >1500 beats (x-axis is time, y-axis is wavelet scale (5 to 300 secs). FIG. 1C illustrates the wavelet amplitudes.

Figure 2A:
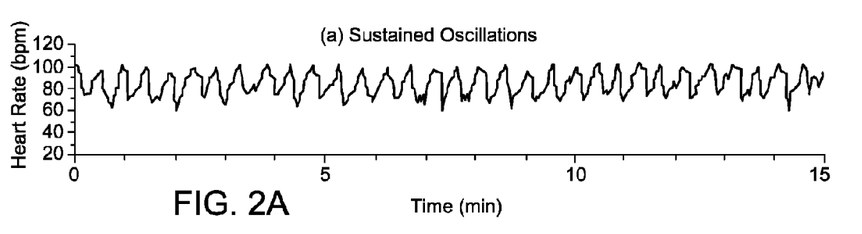
FIGS. 2A-2E illustrate an RR time series demonstrating quantifiable nonlinear dynamics that are distinct within patients with OSA, as illustrated in FIGS. 2A-2C, and also distinct within healthy individuals at high altitude, as illustrated in FIGS. 2D-2E according to an embodiment of the present invention.
Figure 2B:
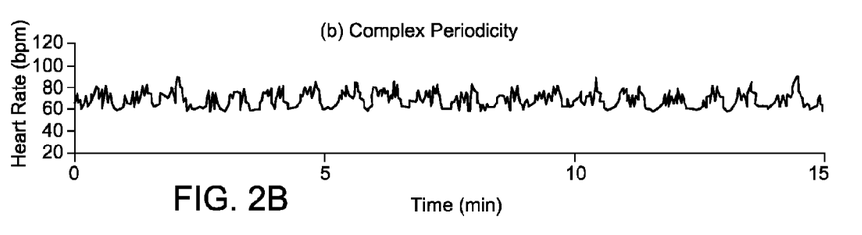
Figure 2C:
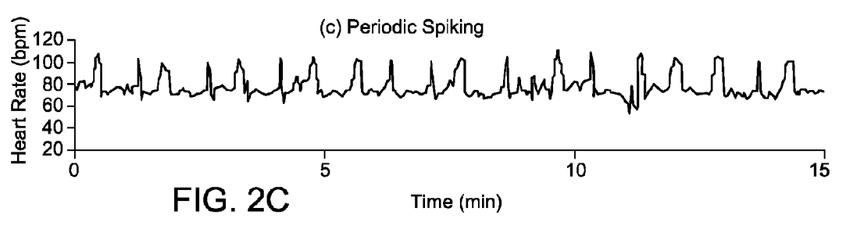
Figure 2D:
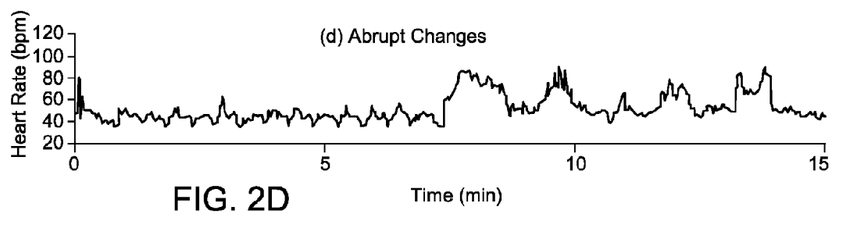
Figure 2E:
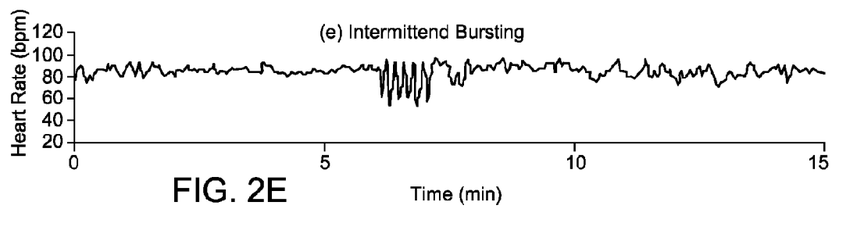

It is quite common for the output of nonlinearly coupled control systems to generate behaviors that defy explanation based on conventional linear models, as illustrated in FIGS. 2A-2E. Characteristic behaviors of nonlinear systems include self-sustained, periodic waves (e.g., ventricular tachycardia), abrupt changes in output (e.g., sudden onset of ventricular fibrillation) and, possibly, chaos. FIGS. 2A-2E illustrate an RR time series demonstrating quantifiable nonlinear dynamics that are distinct within patients with OSA, as illustrated in FIGS. 2A-2C, and also distinct within healthy individuals at high altitude, as illustrated in FIGS. 2D-2E.

On the other hand, nonlinear systems that appear to be very different in their specific details may exhibit certain common output patterns, a characteristic referred to as universality. Moreover, outputs may change in a sudden, discontinuous fashion (e.g., bifurcation), often resulting from a very small change in one of the control modules. For example, the same system may produce a wildly irregular output that becomes highly periodic or vice versa (e.g., electrical alternans, ST-T wave alternans preceding ventricular fibrillation, pulsus alternans during congestive heart failure)

Prior studies have used various nonlinear measures of RR interval complexity, including Poincaré plot, various forms of entropy analysis, and detrended fluctuation analysis to provide insight into heart rate regulatory mechanisms and prediction of adverse events.

The Poincaré plot is a graphical representation of the correlation between successive RR intervals, i.e. plot of RRn+1 as a function of RRn. The significance of this plot is that it is the two-dimensional reconstructed phase space (i.e., the projection of the system attractor that describes the dynamics of the time series). Because an essential feature of this analysis method is the shape of the plot, a common approach used by previous studies has been to parameterize the shape to fit an ellipse oriented according to the line-of-identity (i.e., for a first order plot, RRn=RRn+1). For example, a cigar-shaped plot along the principal diagonal (x=y) would reveal high autocorrelation within the time series, while a circular plot would reveal periodicity (e.g., the Poincaré plot of a sine wave or a pendulum is a circle).

Detrended fluctuation analysis (DFA) is another nonlinear form of analysis to offer insight into temporal dynamics by measuring correlations within the HRV signal. Typically, the correlations are divided into short-term ($\alpha_1$, range 4≤n≤16) and long-term ($\alpha_2$, range 16≤n≤64) fluctuation [0<$\alpha$<0.5 indicates a large value is followed by a small value and vice versa, 0.5<$\alpha$<1.0 indicates a large value is likely to be followed by a large value]. An a value of 0.5, 1.0, >1.0, or >1.5 indicates white noise, 1/f noise, different kinds of noise, or brown noise (integral of white noise), respectively.

Classical information theory, founded by Claude Shannon has been widely utilized for the study of nonlinear signals. Related to thermodynamic entropy, the information entropy can be calculated for any probability distribution (i.e., occurrence of an event that had a probability of occurring out of the space of possible events). The information entropy quantifies the amount of information needed to define the detailed microscopic state of a system, given its macroscopic description, and can be converted into its thermodynamic counterpart based on the Boltzmann distribution. Recent experimental evidence supports this method of conversion.

Shannon entropy (ShanEn) measures information as the decrease of uncertainty at a receiver (or physiological process). ShanEn of the line length distribution is defined as $$ShanEn = \sum_{l_{min}}^{l_{max}} n_l \ln n_l$$

where $n_l$ is the number of length l lines such that $$n_l = \frac{N_l}{\sum_{l'_{min}}^{l'_{max}} N_{l'}}$$

From a chemical thermodynamics perspective, the reduced ΔG would be equal to the minimum number of yes/no questions (using $\log_2$) that needed to be answered in order to fully specify the microscopic state, given the macroscopic state. An increase in Shannon entropy indicates loss of information.

For clinical application to short and noisy time series, another measure "approximate entropy" (ApEn) was developed based on the Kolmogorov entropy, which is the rate of generation of new information. ApEn examines time series for similar epochs such that the presence of more frequent and more similar epochs (i.e., a high degree of regularity) lead to lower ApEn values.

A related method but much more accurate than ShanEn or ApEn is Sample entropy (SampEn), which unlike ApEn, does not count self-matches of templates, does not employ a template-wise strategy for calculating probability and is more reliable for short time series. SampEn is the conditional probability that that two short templates of length m that match within an arbitrary tolerance r will continue to match at the next point m+1.

SampEn is calculated by first forming a set of vectors $u_j$ of length m $$u_j=(RR_j, RR_{j+1}, \ldots, RR_{j+m-1}), j=1,2,\ldots N-m+1$$

where m represents the embedding dimension and N is the number of measured RR intervals. The distance between these vectors is defined as the maximum absolute difference between the corresponding elements $$d(u_j, u_k) = \max[|RR_{j+n}-RR_{k+n}| \| n=0,\ldots,m-1]$$

For each $u_j$, the relative number of vectors $u_k$ for which $d(u_j, u_k) \leq r$ is calculated as $$C_j^m(r) = \frac{nbr \text{ of } [u_k | d(u_j, u_k) \leq r]}{N-m+1} \forall k \neq j$$

with values of $C_j^m(r)$ ranging between 0 and 1. Average of $C_j^m(r)$ yields $$C^m(r) = \frac{1}{N-m+1} \sum_{j=1}^{N-m+1} C_j^m(r)$$

and $$SampEn(m, r, N) = -\ln \frac{C^{m+1}(r)}{C^m(r)}$$

Although the development of SampEn was a major advancement in application of information theory to heart rate dynamics, SampEn has a few significant limitations. What is the optimal value of m? How does one pick r? The usual suggestion is that m should be 1 or 2, noting that there are more template matches and thus less bias for m=1, but that m=2 reveals more of the dynamics of the data. The convention has been that m=2 and r=0.2×SD of the epoch, and these criteria were set on empirical grounds.

COSEn, an optimized form of the SampEn measure, was originally designed and developed at the University of Virginia for the specific purpose of discriminating atrial fibrillation (AF) from normal sinus rhythm (NSR) at all heart rates using very short time series of RR intervals from surface ECGs (i.e., as few as 12 heart beats). As with ApEn and SampEn, smaller values of COSEn indicate a greater likelihood that similar patterns of RR fluctuation will be followed by additional similar measurements. If the time series is highly irregular, the occurrence of similar patterns will not be predictive for the following RR fluctuations and the COSEn value will be relatively large.

Using the same parameters [i.e., length of template or embedding dimension (m)=1], COSEn was subsequently optimized and validated in the Johns Hopkins PROSE-ICD study, requiring only 9 RR intervals before ICD shock to accurately distinguish AF from VT/VF [ROC curve area=0.98 (95% CI:0.93-1.0)] and outperforming representative ICD discrimination algorithms (*Circulation Arrhythmia and Electrophysiology*, in press).

Because nonlinear metrics such as COSEn have better discrimination ability than other conventional methods and the normal sinus rhythm has been shown to reflect health and disease, it would therefore be advantageous to provide a more accurate method for nonlinearly quantifying the self-similar fluctuation patterns in the RR intervals of NSR for prediction of health and mortality.

SUMMARY OF THE INVENTION

The foregoing needs are met, to a great extent, by the present invention, wherein in one aspect a method of nonlinearly determining health and mortality includes obtaining a ventricular activation (RR) time series from a subject for multiple temporal intervals. The method also includes calculating a cardiac entropy in the RR time series over the temporal intervals using coefficient of sample entropy (COSEn). Additionally, the method includes comparing the cardiac entropy between the intervals to determine health and mortality. The absolute and relative changes in entropy over a patient's follow up period provide dynamic information regarding health and mortality risk. The determination of health and mortality can then be used to create a treatment plan for the subject.

The treatment plan created can include monitoring the subject's cardiac rhythms and other physiological signals, including but not limited to respiration, blood pressure, oxygen saturation, temperature and electroencephalogram. The subject can further be one selected from the group consisting of primates, dogs, guinea pigs, rabbits, horses, cats and other organisms.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In accordance with an aspect of the present invention, a method allows for the nonlinear assessment of health and mortality. In order to nonlinearly determine health and mortality, ventricular activation (RR) time series from a subject for a temporal interval are obtained. A first and second cardiac entropy in the RR time series over the temporal interval are determined. The first and second cardiac entropy are compared, to determine health and mortality. This information can then be used to determine a treatment plan for the subject, such as increased monitoring for pathophysiological states.

In accordance with another aspect of the invention, a method is provided for assessing the risk of sudden cardiac death (SCD) by comparing cardiac RR interval rate of entropy change over a predefined time interval for a patient receiving Cardiac Resynchronization Therapy (CRT) to determine changes in entropy of normal sinus rhythm (NSR) and determining increased risk of SCD when the NSR entropy of the patient has increased.

The coefficient of entropy is a calculation of an entropy rate (or entropy) of an RR interval series after it has been unit mean normalized (dividing each observation by the mean of the series). This is analogous to the coefficient of variation, which is the standard deviation after normalization by the mean. In practice, the calculation of the coefficient of entropy is accomplished by subtracting the natural logarithm of the mean from the original entropy calculation. The coefficient of entropy calculated for Q in this way is especially effective and we give it the name coefficient of sample entropy or COSEn for short and denote it by Q*.

The dynamics of cardiac rhythms can be quantified by entropy and entropy rate under the framework of continuous random variables and stochastic processes. The entropy of a continuous random variable X with density $f$ is $$H(X)=E[-\log(f(X))]=\int_{-\infty}^{\infty}-\log(f(x))f(x)dx$$

If X has variance $\sigma^2$, then $Y=X/\sigma$ a has variance 1 and density $\sigma f(\sigma y)$. So the entropy of Y is related to the entropy of X by $$H(Y)=\int_{-\infty}^{\infty}-\log(\sigma f(\sigma y))\sigma f(\sigma y)dy=H(X)-\log(\sigma)$$

which shows that reduced entropy is indicative of reduced variance or increased uncertainty.

Another important property of entropy is provided by the inequality $$H(X) \le \frac{1}{2}(\log(2\pi e) + \log(\sigma^2)) = H(\sigma Z)$$

where Z is a standard Gaussian random variable. This result shows that the Gaussian distribution has maximum entropy among all random variables with the same variance. Thus, an estimate of entropy that is substantially lower than this upper bound for a random sample (with sample variance used as an estimate of $\sigma^2$) provides evidence that the underlying distribution is not Gaussian. This type of distribution is a characteristic of some cardiac arrhythmias, such as bigeminy and trigeminy, that are multimodal and is another reason entropy is important for this application.

Letting X denote the random sequence $X_1, X_2, X_3, \ldots,$ the entropy rate of X is defined as $$H(X) = \lim_{n \to \infty} \frac{H(X_1, X_2, \ldots, X_n)}{n}$$

where the joint entropy of m random variables $X_1, X_2, \ldots, X_m$ is defined as $$H(X_1, X_2, \ldots, X_m) = E[-\log(f(X_1, X_2, \ldots, X_m))]$$

and $f$ is the joint probability density function $f$. For stationary processes, an equivalent definition is $$H(X) = \lim_{m \to \infty} H_m(X) = \lim_{n \to \infty} H(X_{m+1} | X_1, X_2, \ldots, X_m)$$

so entropy rate is the entropy of the conditional distribution of the present observation given the past. The entropy rate for i.i.d. sequences reduces to the entropy of the common distribution.

Estimating the entropy rate for sequences depends on estimates of its densities of order m. Let $X_1, X_2, \ldots, X_n$ denote a stationary random sequence and $X_i(m)$ denote the template consisting of the m×1 vector $(X_{i-m+1}, X_{i-m}, \ldots, X_i)^T$. For notational simplicity, let $X_n = X_n(n)$ denote the whole sequence and $X = X_\infty$ denote the limiting infinite sequence. The sequence $X_m(m), X_{m+1}(m), \ldots, X_n(m)$ is not independent, but many methods developed to analyze independent vector data are applicable. In particular, the $m^{th}$-order probability density function of the sequence, $f$, and entropy $$E[-\log(f(X_1, X_2, \ldots, X_m))]$$

can still be estimated empirically. These are the fundamental calculations in ApEn and SampEn.

We define the COSEn as the sample entropy of a series after being normalized by the mean. This is equivalent to subtracting the natural logarithm of the mean from the original entropy. To see this, note that if X has mean μ, then Y=X/μ has mean 1 and density μ$f$(μy). So the entropy of Y is related to the entropy of X by $$H(Y) = \int_{-\infty}^{\infty} -\log(\mu f(\mu y)) \mu f(\mu y) dy = H(X) - \log(\mu)$$

as stated. Similar results can be shown for all Renyi entropy rates and in particular for the differential quadratic entropy rate Q calculated using the SampEn algorithm. This leads to the calculation $$Q^* = Q - \log(\mu)$$

where $Q^*$ is the coefficient of sample entropy.

Figure 3:
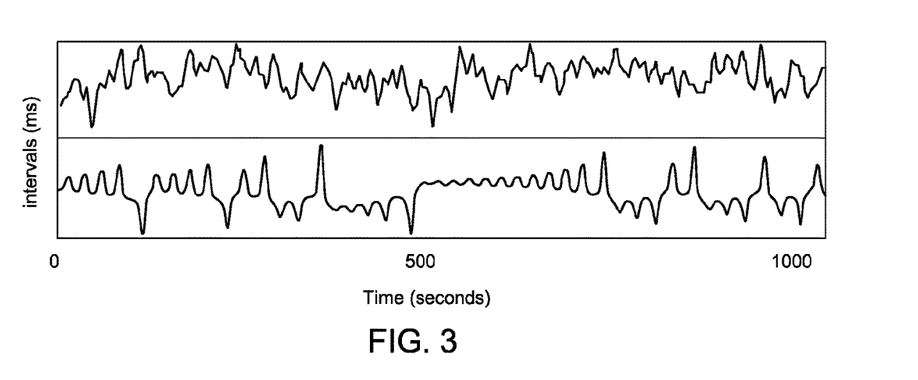
FIG. 3 shows analysis of heart rate variability.

Current clinical measures, including ECG metrics, are insufficient for SCD risk stratification, and the effect of CRT on SCD is debated. Little is known about the prognostic value of ECG entropy in short-term time series of RR and QT intervals. Entropy is fundamentally different from heart rate variability (HRV) in that entropy quantifies the degree to which heart rate fluctuation patterns repeat themselves. As shown in FIG. 3, "self-similar" fluctuations in heart rate are indistinguishable in moment statistics and frequency domain measures of HRV.

In accordance with the invention, RR intervals were collected from 5-min surface ECGs of 134 consecutive patients who were in NSR at time of biventricular ICD implantation (baseline), and at 6-month clinic visits (4±2 mean number of visits) until ICD shock if occurred (N=44; 6±5 mo). The patients (age 51±12 yrs, male 66%, white 82%, DM 26%, HTN 46%, ICM 32%, EF 20±8%, NYHA class 2.3±0.8) were well treated medically for heart failure. Entropy was measured using coefficient of sample entropy (COSEn), based on Kolmogorov-Sinai entropy with roots in chaos theory. For each patient, rate of entropy change (δE/δt) was measured as the slope of linear regression fit to values at baseline and subsequent clinic visits excluding shock. ICD shocks or deaths from ventricular tachyarrhythmias (VT/VF) were used as a specific surrogate for SCD.

Figure 4:
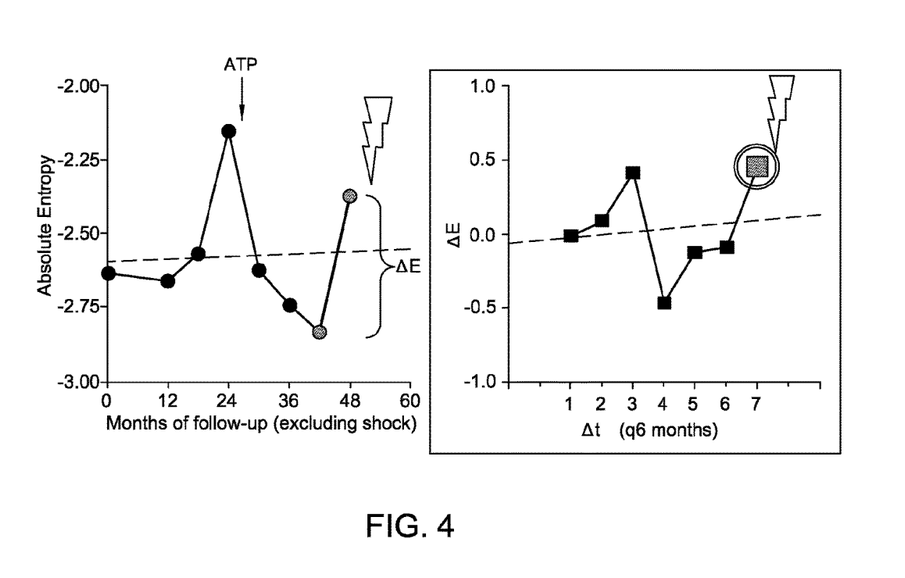
FIG. 4 shows graphs of calculated change in entropy over time for patients at risk of SCD, in accordance with an aspect of the invention.
Figure 5:
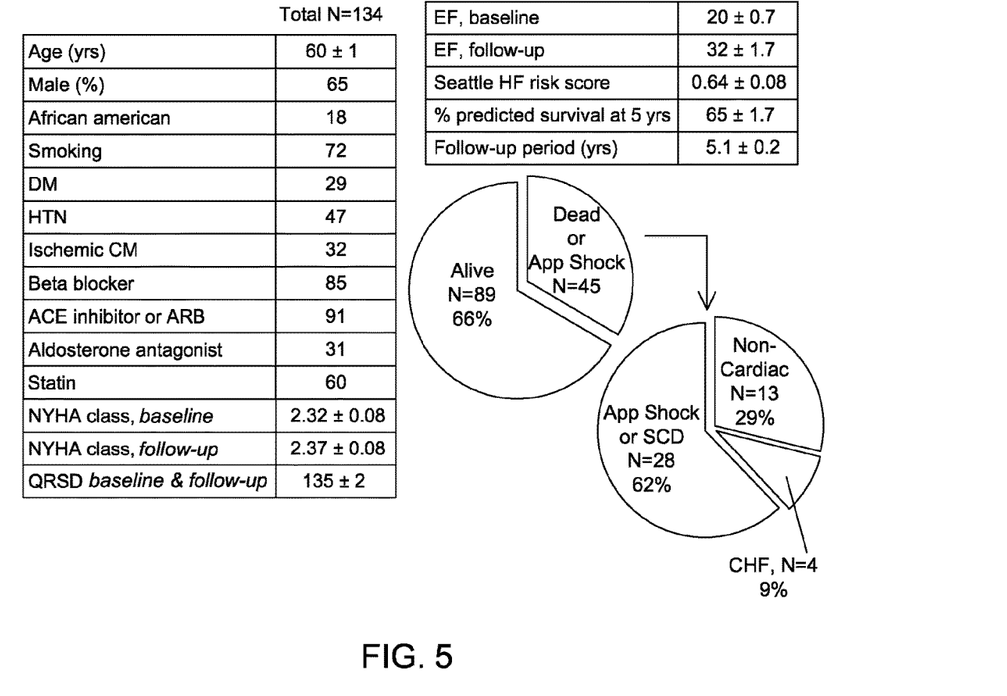
FIG. 5 is a diagram illustrating vital demographics of patients in an observational study in accordance with the invention.
Figure 6:
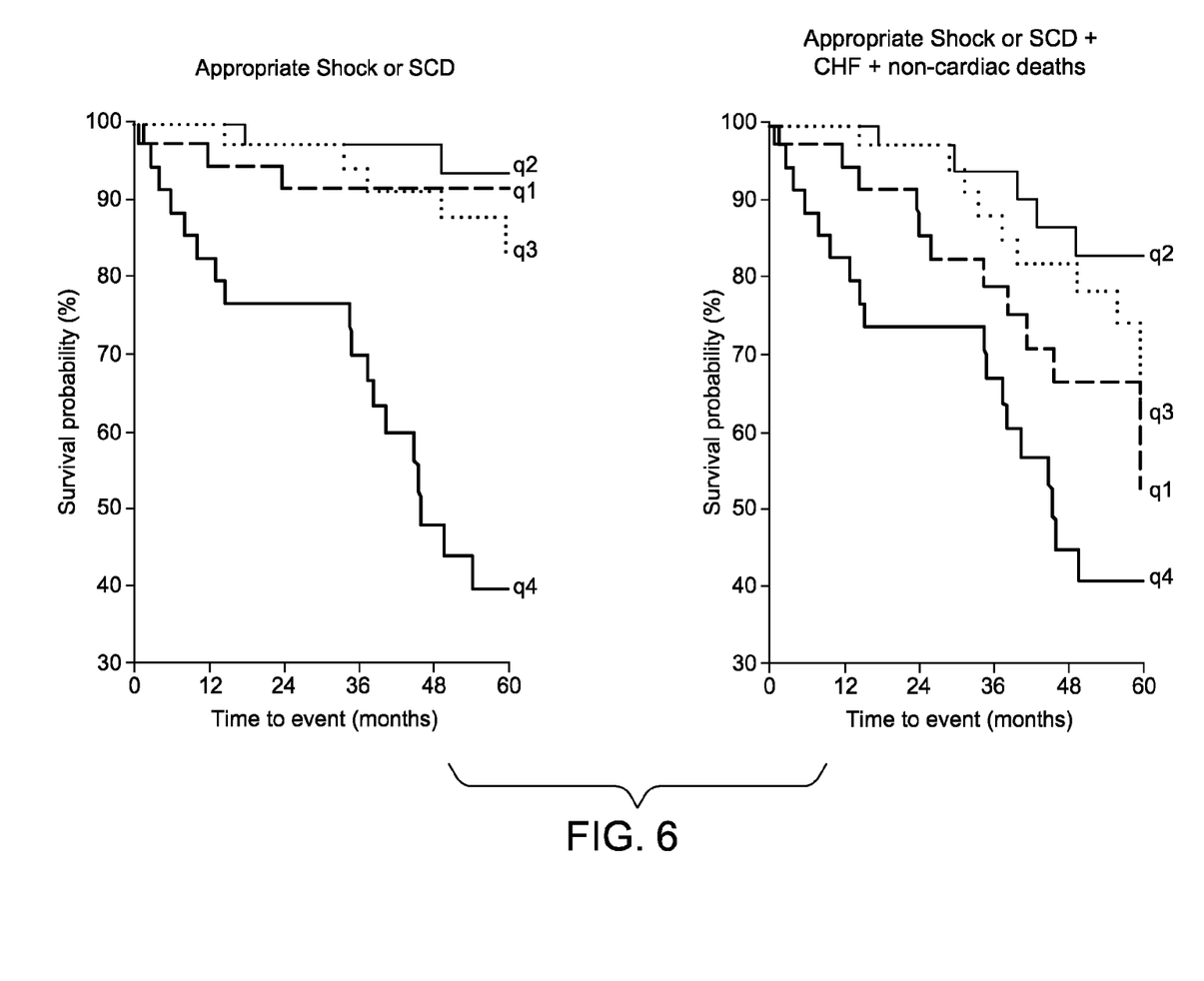
FIG. 6 shows Kaplan-Meier survival curves for the patients in FIG. 5.
Figure 7:
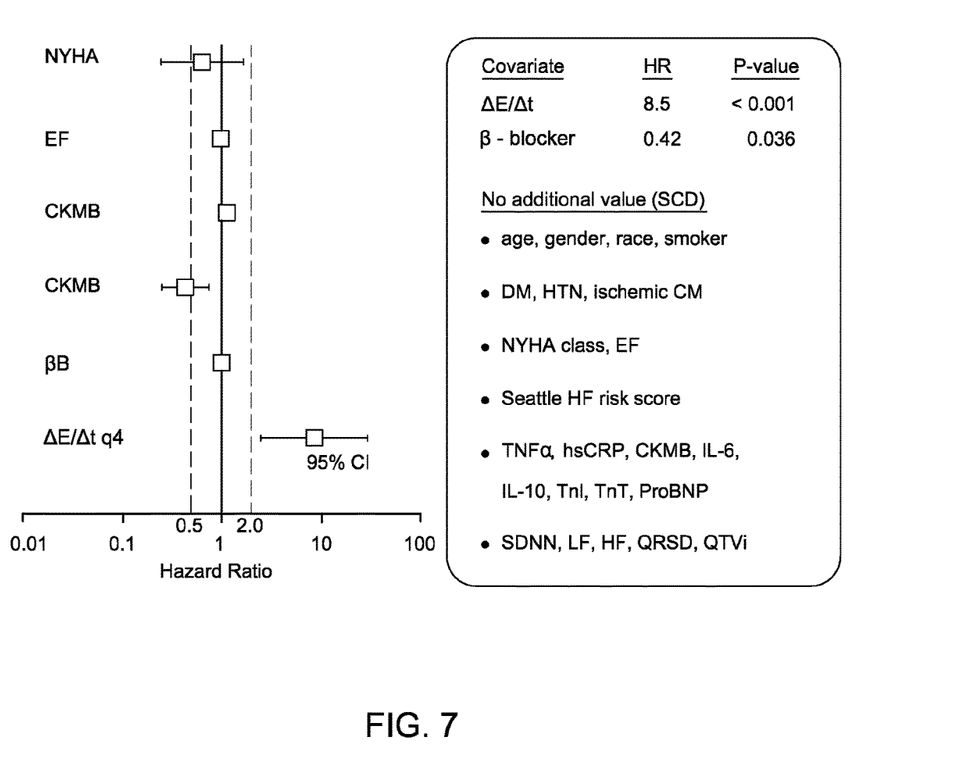
FIG. 7 shows Hazard Ratios for multiple parameters of SCD patients.
Figure 8:
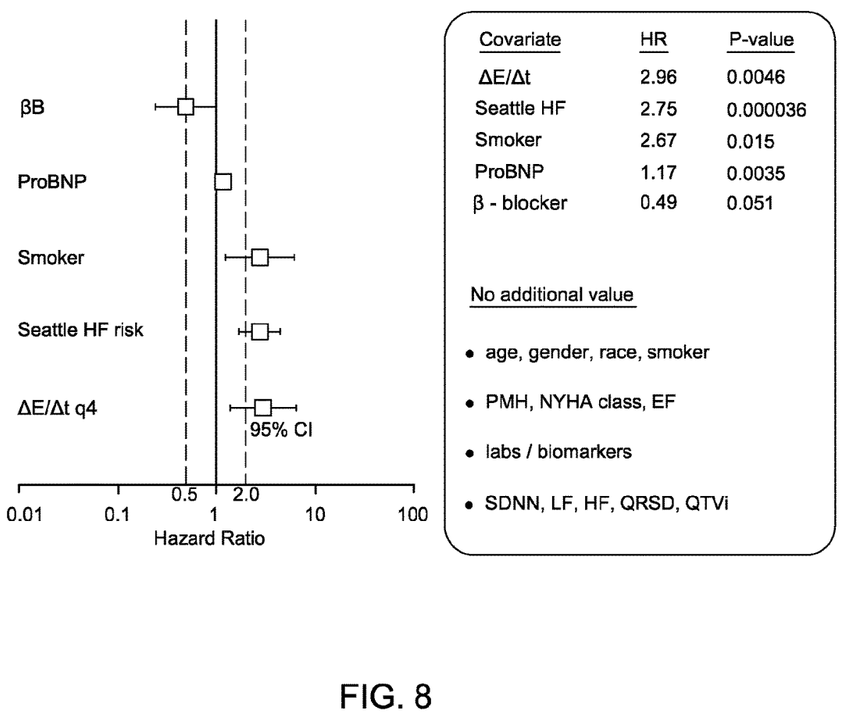
FIG. 8 shows Hazard Ratios for multiple parameters of patient death in the study due to all causes.

As shown in FIG. 4, for each patient, entropy change was measured as ΔE/Δt, the change in entropy over two routine 6 month clinical visits preceding an ICD shock (and excluding the clinical visit after the ICD shock). As shown, the ΔE/Δt for the time interval preceding an ICD shock was a strong predictor of increased risk of SCD (where ICD shock is used as a surrogate for SCD). FIG. 5 is a graph illustrating the demographics of the N=134 patients. Of the N=45 patients who died or experienced ICD shock, N=28 or 62% experienced ICD shock or died from SCD. FIG. 6 shows Kaplan-Meier curves for these patients, per quartile of ΔE/Δt. As shown, patients in the $4^{th}$ quartile for ΔE/Δt had the lowest survival probability. FIG. 7 shows hazard ratios for SCD for multiple parameters, and FIG. 8 shows hazard ratios for all deaths for multiple parameters. As shown, ΔE/Δt alone as a predictor had a confidence interval (CI) of 95%.

Over 53±22 months of follow-up, entropy rose in patients who had shocks for VT/VF (δE/δt=+0.025±0.041/mo) but fell in those with no shocks (−0.0075±0.039) or only inappropriate shocks (−0.013±0.025; p=0.002). In contrast, there were no significant changes in heart rate or heart rate variability analyses (i.e., SDNN, RMSSD). In multivariate analyses, δE/δt was the strongest predictor of SCD (p<0.001) after taking age, gender, risk factors, NYHA class, duration of follow-up, medications, biomarkers, and ejection fraction into account. The C-statistic for δE/δt alone was 0.73 (p<0.001), a multivariable model using the clinical variables was 0.77 (p=0.019), and a model using all parameters was 0.86 (p<0.001), suggesting an entropy-based measure has utility in clinical care.

Figure 9:
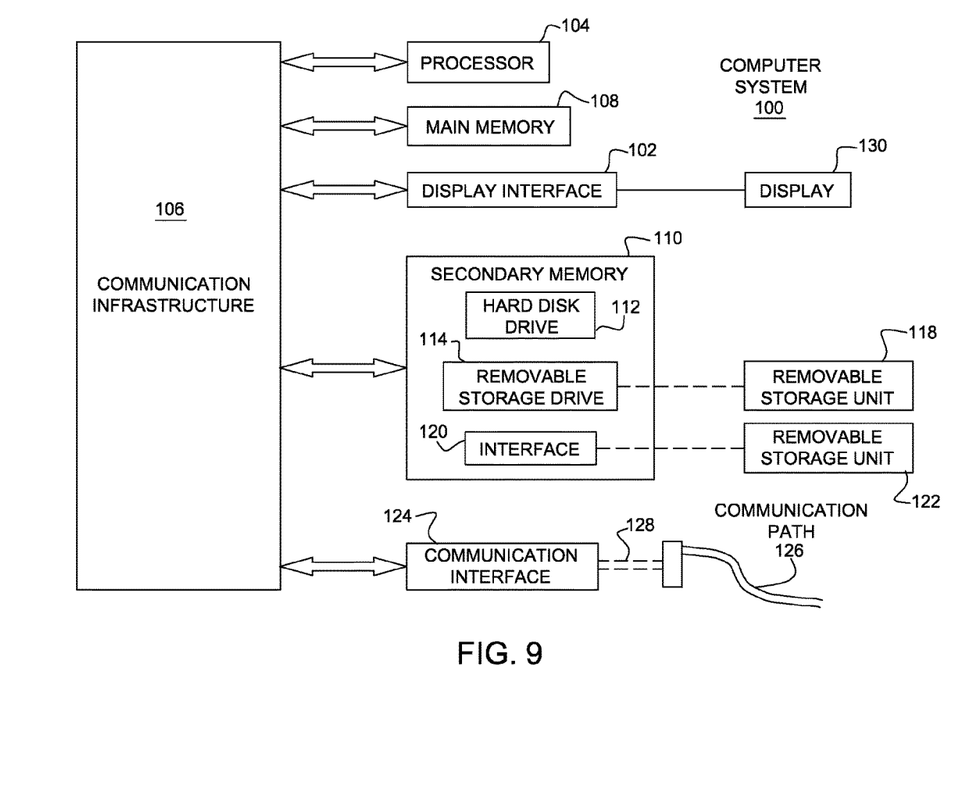
FIG. 9 is a block diagram of an illustrative computer system capable of implementing the methods of the present invention.

Turning to FIG. 9, it is contemplated that embodiments of the invention may be practiced using a computer system. FIG. 9 is an illustrative block diagram for a computer system 100 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs). In an example embodiment, the invention was implemented in software running on a general purpose computer 100 as illustrated in FIG. 1. The computer system 100 may include one or more processors, such as processor 104. The Processor 104 is connected to a communication infrastructure 106 (e.g., a communications bus, cross-over bar, or network). The computer system 100 may include a display interface 102 that forwards graphics, text, and other data from the communication infrastructure 106 (or from a frame buffer not shown) for display on the display unit 830.

The computer system 10 may also include a main memory 108, preferably random access memory (RAM), and may include a secondary memory 110. The secondary memory 110 may include, for example, a hard disk drive 112 and/or a removable storage drive 114, representing a floppy disk drive, a magnetic tape drive, an optical disk drive, a flash memory, etc. The removable storage drive 114 reads from and/or writes to a removable storage unit 118 in a well-known manner. Removable storage unit 118, represents a floppy disk, magnetic tape, optical disk, etc. which is read by and written to by removable storage drive 114. As will be appreciated, the removable storage unit 118 includes a computer usable storage medium having stored therein computer software and/or data.

In alternative embodiments, secondary memory 110 may include other means for allowing computer programs or other instructions to be loaded into computer system 100. Such means may include, for example, a removable storage unit 122 and an interface 120. Examples of such removable storage units/interfaces include a program cartridge and cartridge interface (such as that found in video game devices), a removable memory chip (such as a ROM, PROM, EPROM or EEPROM) and associated socket, and other removable storage units 122 and interfaces 120 which allow software and data to be transferred from the removable storage unit 122 to computer system 100.

The computer system 100 may also include a communications interface 124. Communications interface 124 allows software and data to be transferred between computer system 100 and external devices. Examples of communications interface 824 may include a modem, a network interface (such as an Ethernet card), a communications port (e.g., serial or parallel, etc.), a PCMCIA slot and card, a modem, etc. Software and data transferred via communications interface 124 are in the form of signals 828 which may be electronic, electromagnetic, optical or other signals capable of being received by communications interface 124. Signals 128 are provided to communications interface 124 via a communications path (i.e., channel) 126. Channel 126 (or any other communication means or channel disclosed herein) carries signals 128 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as removable storage drive 114, a hard disk installed in hard disk drive 112, and signals 128. These computer program products are means for providing software to computer system 100. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) may be stored in main memory 108 and/or secondary memory 110. Computer programs may also be received via communications interface 124. Such computer programs, when executed, enable computer system 100 to perform the features of the present invention as discussed herein. In particular, the computer programs, when executed, enable processor 104 to perform the functions of the present invention. Accordingly, such computer programs represent controllers of computer system 100.

In an embodiment where the invention is implemented using software, the software may be stored in a computer program product and loaded into computer system 100 using removable storage drive 114, hard drive 112 or communications interface 124. The control logic (software), when executed by the processor 104, causes the processor 104 to perform the functions of the invention as described herein.

The features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A method for determining increased risk of mortality of a patient, comprising:
   measuring a first cardiac rhythm of a patient at a first time;
   identifying at least one segment of said first cardiac rhythm;
   calculating a first entropy measurement for the at least one segment;
   measuring a second cardiac rhythm of said patient at a second time subsequent to said first time;
   identifying at least one segment of said second cardiac rhythm;
   calculating a second entropy measurement for the at least one segment of said second cardiac rhythm;
   calculating a change in entropy by comparing said second entropy measurement with said first entropy measurement; and
   determining that said patient is at an increased risk of mortality when said change in entropy is above a predetermined value.

2. The method of claim 1, wherein the entropy measurement is a measurement of absolute entropy.

3. The method of claim 2, wherein the absolute entropy measurement is a coefficient of sample entropy (COSEn).

4. The method of claim 3, wherein the at least one cardiac rhythm arises from at least a deterministic process.

5. The method of claim 3, wherein the at least one cardiac rhythm arises from a combination of both deterministic and stochastic physiological processes.

6. The method of claim 3, wherein the at least one segment comprises a series of beats having a statistically homogeneous time interval between beats.

7. The method of claim 4, wherein each at least one cardiac rhythm comprises a heart rate time series such as would be provided by non-invasive devices that do not use a conventional ECG signal.

8. The method of claim 3, wherein the heart rate time series comprises a number of beats, and wherein COSEn is calculated at least every 50 beats.

9. The method of claim 3, wherein the at least one cardiac rhythm comprises an RR-interval series, and wherein the step of calculating COSEn for at least one segment comprises:
    calculating a mean RR-interval for the RR-interval series;
    using the mean RR-interval as a continuous variable;
    unit mean normalizing the RR-interval series by dividing each observation by the mean RR-interval; and
    calculating COSEn as an entropy rate or entropy of the unit mean normalized RR interval series.

10. The method of claim 3, wherein the at least one cardiac rhythm comprises an RR-interval series, and wherein the step of calculating COSEn for at least one segment comprises:
    calculating the differential quadratic entropy rate using a sample entropy (SampEn) algorithm;
    calculating a mean RR-interval for the RR-interval series; and
    subtracting the natural logarithm of the mean RR-interval from the differential quadratic entropy rate to obtain COSEn.

11. The method of claim 1, wherein said first cardiac rhythm is measured when said patient is in normal sinus rhythm (NSR).

12. The method of claim 1, wherein said second time is on the order of months subsequent to said first time.

13. The method of claim 1, wherein calculation of a change in entropy comprises calculating a rate of entropy change.

14. The method of claim 13, wherein calculation of a rate of entropy change comprises measuring a slope of a linear regression fit to values at a baseline measurement and subsequent measurements of cardiac rhythm.

15. The method of claim 11, wherein said change in entropy is a rising entropy of NSR.

16. The method of claim 1, wherein determining that said patient is at increased risk of mortality further comprises use of a multivariable model that employs entropy measures.

17. An apparatus comprising:
    a programmable computer, programmed to
    measure a first cardiac rhythm of a patient at a first time;
    identify at least one segment of said first cardiac rhythm;
    calculate a first entropy measurement for the at least one segment;
    measure a second cardiac rhythm of said patient at a second time subsequent to said first time;
    identify at least one segment of said second cardiac rhythm;
    calculate a second entropy measurement for the at least one segment of said second cardiac rhythm; and
    calculate a change in entropy by comparing said second entropy measurement with said first entropy measurement.

18. The apparatus of claim 17, wherein the entropy measurement is a measurement of absolute entropy.

19. The apparatus of claim 18, wherein the absolute entropy measurement is a coefficient of sample entropy (COSEn).

20. The apparatus of claim 19, wherein the at least one cardiac rhythm comprises an RR-interval series, and wherein calculating COSEn for at least one segment comprises:
    calculating a mean RR-interval for the RR-interval series;
    using the mean RR-interval as a continuous variable;
    unit mean normalizing the RR-interval series by dividing each observation by the mean RR-interval; and
    calculating COSEn as an entropy rate or entropy of the unit mean normalized RR interval series.

21. The apparatus of claim 19, wherein the at least one cardiac rhythm comprises an RR-interval series, and wherein calculating COSEn for at least one segment comprises:
    calculating the differential quadratic entropy rate using a sample entropy (SampEn) algorithm;
    calculating a mean RR-interval for the RR-interval series; and
    subtracting the natural logarithm of the mean RR-interval from the differential quadratic entropy rate to obtain COSEn.

22. The apparatus of claim 17, wherein said first cardiac rhythm is measured when said patient is in normal sinus rhythm (NSR).

23. The apparatus of claim 17, wherein said second time is on the order of months subsequent to said first time.

24. The apparatus of claim 17, wherein calculation of a change in entropy comprises calculating a rate of entropy change.

25. The apparatus of claim 24, wherein calculation of a rate of entropy change comprises measuring a slope of a linear regression fit to values at a baseline measurement and subsequent measurements of cardiac rhythm.

26. The apparatus of claim 22, wherein said change in entropy is a rising entropy of NSR.

27. A computer program product comprising a non-transient computer readable storage medium storing computer-executable instructions causing a computer to:
    receive a measurement of a first cardiac rhythm of a patient taken at a first time;
    identify at least one segment said first cardiac rhythm;
    calculate a first entropy measurement for the at least one segment;
    receive a measurement of a second cardiac rhythm of said patient taken at a second time subsequent to said first time;
    identify at least one segment of said second cardiac rhythm;
    calculate a second entropy measurement for the at least one segment of said second cardiac rhythm; and
    calculate a change in entropy by comparing said second entropy measurement with said first entropy measurement.

* * * * *